United States Patent [19]

Anderson et al.

[11] Patent Number: 4,469,872

[45] Date of Patent: Sep. 4, 1984

[54] SUBSTITUTED PYRIDYLOXYPHENOXYHYDROXYKETONES

[75] Inventors: Richard J. Anderson, Palo Alto; Shy-Fuh Lee, Sunnyvale, both of Calif.

[73] Assignee: Zoecon Corporation, Palo Alto, Calif.

[21] Appl. No.: 410,172

[22] Filed: Aug. 20, 1982

[51] Int. Cl.³ .......................................... C07D 213/64
[52] U.S. Cl. .................................. 546/302; 546/157; 546/291; 546/301; 546/312; 544/354; 548/166; 548/221; 568/308; 568/325
[58] Field of Search ............... 546/301, 302, 312, 291

[56] References Cited

U.S. PATENT DOCUMENTS

| | | | |
|---|---|---|---|
| 3,379,752 | 4/1968 | Bolhofer | 260/473 |
| 4,134,751 | 1/1979 | Nishiyama | 71/94 |
| 4,216,007 | 8/1980 | Nishiyama | 71/94 |
| 4,348,221 | 9/1982 | Szczepanski | 71/94 |

Primary Examiner—Alan L. Rotman
Attorney, Agent, or Firm—Jacqueline S. Larson; Donald W. Erickson

[57] ABSTRACT

Substituted phenoxyhydroxyketones, intermediates therefor, synthesis thereof, and the use of said compounds for the control of weeds.

7 Claims, No Drawings

SUBSTITUTED PYRIDYLOXYPHENOXYHYDROXYKETONES

This invention relates to substituted phenoxyhydroxyketones and derivatives thereof, intermediates therefor, synthesis thereof, and the use of said compounds for the control of weeds.

More particularly, the compounds of the present invention are represented by the following formulas (A) and (B):

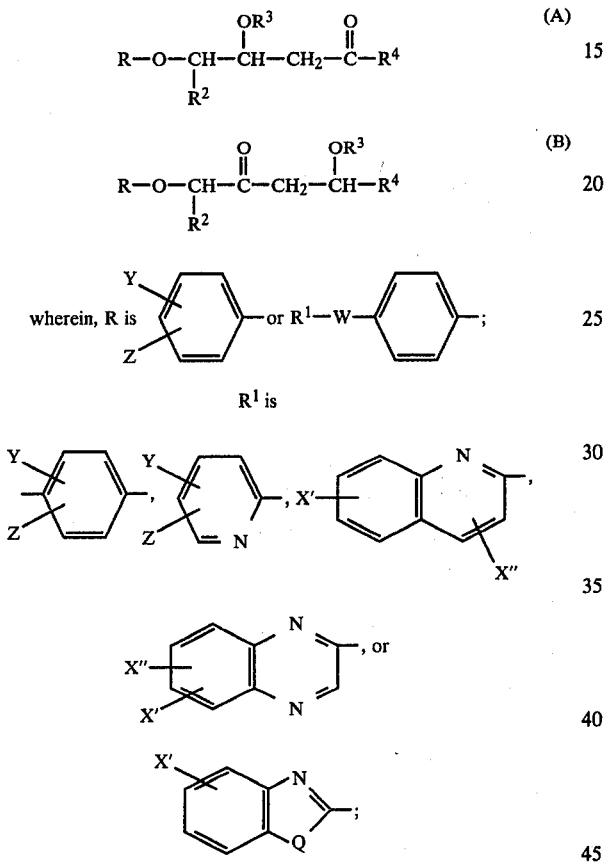

$R^2$ is hydrogen or lower alkyl;
$R^3$ is hydrogen, lower alkyl,

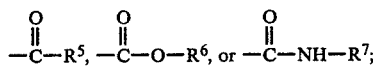

$R^4$ is lower alkyl;
$R^5$ is lower alkyl, lower haloalkyl, substituted or unsubstituted phenyl, substituted or unsubstituted benzyl, or substituted or unsubstituted phenoxyalkyl;
$R^6$ is lower alkyl;
$R^7$ is hydrogen, lower alkyl or substituted or unsubstituted phenyl; W is oxygen, sulfur or amino;
Q is oxygen, sulfur or amino;
each of Y and Z is independently selected from hydrogen, lower alkyl, lower haloalkyl, lower alkoxy, lower haloalkoxy, halogen, nitro and cyano; and
each of X' and X" is independently selected from hydrogen, lower haloalkyl, lower alkoxy, halogen and nitro, provided that both X' and X" cannot be trifluoromethyl, methoxy or nitro.

In the description and claims hereinafter, each of $R$—$R^7$, Q, W, X', X" and Y and Z is as defined above, unless otherwise specified.

Compounds of the present invention of formula (A') (A where $R^3$ is hydrogen) can be prepared from an aldehyde (I) and an anion of the dimethylhydrazone of an appropriate ketone (II) following the method described by E. J. Corey and D. Enders, Tetrahedron Letters, 3–6 (1976) and Tetrahedron Letters, 11–14 (1976).

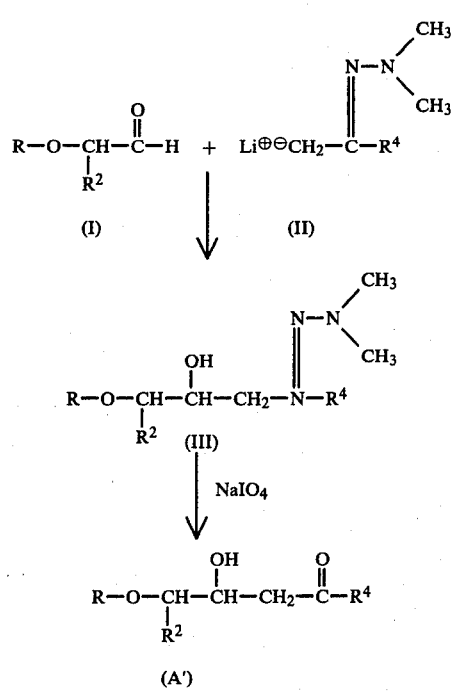

By the same general methods, compounds of the present invention of formula (B') (B where $R^3$ is hydrogen) can be prepared from an anion of a dimethylhydrazone of formula (IV) and an aldehyde (V).

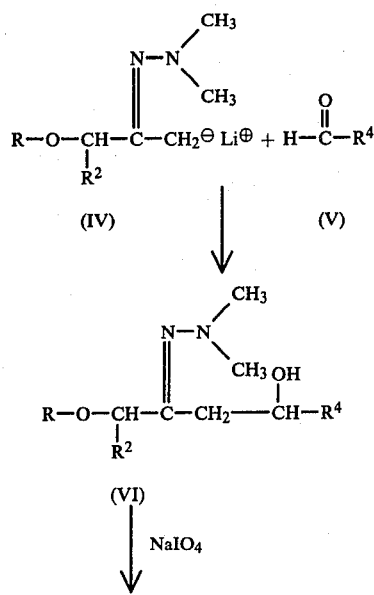

-continued

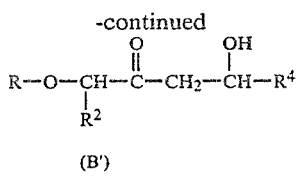

(B')

The dimethylhydrazone anion (II) or (IV) can be prepared by reacting the appropriate ketone precursor with N,N-dimethylhydrazine [cf., A. C. Day and M. Whiting, Org. Synthesis 50:3 (1970)], and treating the resulting dimethylhydrazone of the ketone with n-butyllithium and tetrahydrofuran (THF) or with lithiumdiisopropylamide (LDA) and THF at a low temperature.

Compounds of formula (A) or (B) where $R^3$ is

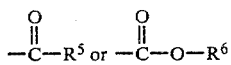

can be synthesized by reacting a hydroxyketone of formula (A') or (B') with the appropriate carbonyl halide or alkoxycarbonyl halide in an organic solvent such as benzene and with or without a catalyst such as pyridine, avoiding strongly acid or base conditions.

Compounds of formula (A) or (B) where $R^3$ is

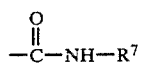

can be prepared by reacting a hydroxyketone of formula (A') or (B') with $R^7$—N=C=O in an organic solvent.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "phenoxyalkyl" refers to a lower alkyl group substituted with a phenoxy group.

The terms "substituted phenyl," "substituted benzyl" and "substituted phenoxyalkyl" refer to a phenyl group, a benzyl group and a phenoxyalkyl group, respectively, substituted at one, two or three of the ring carbon atoms with a group selected from lower alkyl, lower haloalkyl, lower alkoxy, halogen, nitro and cyano.

The compounds of the present invention have one or more asymmetric carbon atoms. The present invention includes each of the optically active isomers and racemic mixtures thereof. In the examples hereinafter, unless otherwise specified, the compound prepared is a racemic mixture.

The novel compounds of formulas (A) and (B) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds. Grass plant (weed) species on which the compounds of the present invention show effective herbicidal activity include shattercane, crabgrass, sprangletop, wild oats, bermudagrass, tall fescue, rice, wheat, barley, corn, blue panicum, foxtails, rough bluegrass, winter rye, annual ryegrass, watergrass and Johnsongrass. It appears to be most effective to apply the active compound prior to the heading stage of the grass weed.

Methods of preparing herbicidal formulations which can be used with a compound of the present invention are described in the literature along with suitable liquid and solid carriers, such as in U.S. Pat. No. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal acticity, can be advantageously combined with broadleaf weed herbicides for broadspectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

To a solution of acetone N,N-dimethylhydrazone (6.5 mmol) in tetrahydrofuran (THF; 15 ml) under nitrogen is added lithium diisopropylamide (LDA; 7.2 mmol) in THF (15 ml) at 0° for 5 hours. The resulting solution is cooled to −78°, and to it is added 2-[4-(4-trifluoromethylphenoxy)phenoxy]propanal (7.2 mmol). After 1 hour at −78°, the reaction mixture is allowed to warm to 0° and is poured into water/methylene chloride (3:1). The organic phase is separated (3X), and the combined organic extracts are dried over sodium sulfate and concentrated to give 4-hydroxy-5-[4-(4-trifluoromethylphenoxy)-phenoxy]-2-hexanone N,N-dimethylhydrazone (cpd. 1, Table A).

4-Hydroxy-5-[4-(4-trifluoromethylphenoxy)phenoxy]-2-hexanone N,N-dimethylhydrazone (1 mmol) is dissolved in methanol (15 ml) and 1.0 N pH 7 phosphate buffer (3 ml), and a solution of sodium periodate (2.2 mmol) in water (5 ml) is added at 25° with stirring. After about 3 hours, the reaction mixture is filtered, poured into water and extracted with methylene chloride. The extract is dried and concentrated in vacuo to give 4-hydroxy-5-[4-(4-trifluoromethylphenoxy)phenoxy]-2-hexanone (cpd. 1, Table B).

EXAMPLE 2

Following the procedure of Example 1, the lithium salt of acetone N,N-dimethylhydrazone is reacted with each of the aldehydes under column I to give the corresponding compound in Table A, which is then hydrolyzed to the corresponding ketone in Table B.

I 2. 2-[4-(2-chloro-4-trifluoromethylphenoxy)phenoxy]propanal.
3. 2-[4-(2,4-dichlorophenoxy)phenoxy]propanal.
4. 2-[4-(2-nitro-4-trifluoromethylphenoxy)phenoxy]propanal.
5. 2-[4-(2-fluoro-4-trifluoromethylphenoxy)phenoxy]propanal.
6. 2-[4-(4-trifluoromethylphenylthio)phenoxy]propanal.
7. 2-[4-(2-nitro-4-trifluoromethylanilino)phenoxy]propanal.
8. 2-[4-(4-trifluoromethylphenoxy)phenoxy]ethanal.

EXAMPLE 3

Following the procedure of Example 1, 2-[4-(4-trifluoromethylphenoxy)phenoxy]propanal is reacted with the lithium salt of 2-butanone N,N-dimethylhydrazone to give 5-hydroxy-6-[4-(4-trifluoromethylphenoxy)phenoxy]-3-heptanone N,N-dimethylhydrazone (cpd. 9, Table A). This hydrazone is then hydrolyzed to 5-hydroxy-6-[4-(4-trifluoromethylphenoxy)phenoxy]-3-heptanone (cpd. 9, Table B).

EXAMPLE 4

To 4-hydroxy-5-[4-(4-trifluoromethylphenoxy)phenoxy]-2-hexanone (3.5 mmol) and pyridine (3.5 mmol) in benzene (20 ml) is added acetyl chloride (4.0 mmol). The mixture is stirred at RT overnight. The reaction mixture is diluted with benzene, washed with water, dried and the solvent is removed in vacuo to give 4-acetoxy-5-[4-(4-trifluoromethylphenoxy)phenoxy]-2-hexanone (cpd. 10, Table B).

Following the same procedure, each of the compounds under column II is reacted with 4-hydroxy-5-[4-(4-trifluoromethylphenoxy)phenoxy]-2-hexanone to give the corresponding ketones in Table B.

II 11. 2,2-dichloropropionyl chloride.
12. 4-(2,4-dichlorophenoxy)butyryl chloride.
13. ethoxycarbonyl chloride.
14. ethyl isocyanate.

TABLE A

Z—⟨Y-phenyl⟩—W—⟨phenyl⟩—O—CH(R²)—CH(OR³)—CH₂—C(=N-N(CH₃)CH₃)—R⁴

| Cpd. | Z | Y | W | R² | R³ | R⁴ |
|---|---|---|---|---|---|---|
| 1 | CF₃ | H | O | CH₃ | H | CH₃ |
| 2 | CF₃ | Cl | O | CH₃ | H | CH₃ |
| 3 | Cl | Cl | O | CH₃ | H | CH₃ |
| 4 | CF₃ | NO₂ | O | CH₃ | H | CH₃ |
| 5 | CF₃ | F | O | CH₃ | H | CH₃ |
| 6 | CF₃ | H | S | CH₃ | H | CH₃ |
| 7 | CF₃ | NO₂ | NH | CH₃ | H | CH₃ |

TABLE A-continued

| Cpd. | Z | Y | W | R² | R³ | R⁴ |
|---|---|---|---|---|---|---|
| 8 | CF₃ | H | O | H | H | CH₃ |
| 9 | CF₃ | H | O | CH₃ | H | CH₂CH₃ |

TABLE B

Z—⟨Y-phenyl⟩—W—⟨phenyl⟩—O—CH(R²)—CH(OR³)—CH₂—C(=O)—R⁴

| Cpd | Z | Y | W | R² | R³ | R⁴ |
|---|---|---|---|---|---|---|
| 1 | CF₃ | H | O | CH₃ | H | CH₃ |
| 2 | CF₃ | Cl | O | CH₃ | H | CH₃ |
| 3 | Cl | Cl | O | CH₃ | H | CH₃ |
| 4 | CF₃ | NO₂ | O | CH₃ | H | CH₃ |
| 5 | CF₃ | F | O | CH₃ | H | CH₃ |
| 6 | CF₃ | H | S | CH₃ | H | CH₃ |
| 7 | CF₃ | NO₂ | NH | CH₃ | H | CH₃ |
| 8 | CF₃ | H | O | H | H | CH₃ |
| 9 | CF₃ | H | O | CH₃ | H | CH₂CH₃ |
| 10 | CF₃ | H | O | CH₃ | C(O)CH₃ | CH₃ |
| 11 | CF₃ | H | O | CH₃ | C(O)C(Cl)₂CH₃ | CH₃ |
| 12 | CF₃ | H | O | CH₃ | C(O)(CH₂)₃OC₆H₃—(2,4-diCl) | CH₃ |
| 13 | CF₃ | H | O | CH₃ | C(O)OCH₂CH₃ | CH₃ |
| 14 | CF₃ | H | O | CH₃ | C(O)NHCH₂CH₃ | CH₃ |

EXAMPLE 5

Following the procedure of Example 1, the lithium salt of acetone N,N-dimethylhydrazone is reacted with each of the propanals under column III to give the N,N-dimethylhydrazone of the β-hydroxy ketone, which is then hydrolyzed to the corresponding ketone under column IV.

III 15. 2-[4-(3-chloro-5-trifluoromethyl-2-pyridyloxy)phenoxy]-propanal.
16. 2-[4-(3,5-dichloro-2-pyridyloxy)phenoxy]propanal.
17. 2-[4-(5-trifluoromethyl-2-pyridyloxy)phenoxy]propanal.
18. 2-[4-(6-fluoro-2-quinolyloxy)phenoxy]propanal.
19. 2-[4-(6-chloro-2-quinolyloxy)phenoxy]propanal.
20. 2-[4-(6-fluoro-2-quinoxalinyloxy)phenoxy]propanal.
21. 2-[4-(6-chloro-2-quinoxalinyloxy)phenoxy]propanal.
22. 2-[4-(6-trifluoromethyl-2-quinoxalinyloxy)phenoxy]propanal.
23. 2-[4-(6-chloro benzo-1,3-oxazolyl-2-oxy)phenoxy]propanal.
24. 2-[4-(6-chloro benzo-1,3-thiazolyl-2-oxy)phenoxy]propanal.

IV 15. 4-hydroxy-5-[4-(3-chloro-5-trifluoromethyl-2-pyridyloxy)-phenoxy]-2-hexanone.
16. 4-hydroxy-5-[4-(3,5-dichloro-2-pyridyloxy)phenoxy]-2-hexanone.
17. 4-hydroxy-5-[4-(5-trifluoromethyl-2-pyridyloxy)phenoxy]-2-hexanone.

18. 4-hydroxy-5-[4-(6-fluoro-2-quinolyloxy)phenoxy]-2-hexanone.
19. 4-hydroxy-5-[4-(6-chloro-2-quinolyloxy)phenoxy]-2-hexanone.
20. 4-hydroxy-5-[4-(6-fluoro-2-quinoxalinyloxy)phenoxy]-2-hexanone.
21. 4-hydroxy-5-[4-(6-chloro-2-quinoxalinyloxy)phenoxy]-2-hexanone.
22. 4-hydroxy-5-[4-(6-trifluoromethyl-2-quinoxalinyloxy)phenoxy]-2-hexanone.
23. 4-hydroxy-5-[4-(6-chloro benzo-1,3-oxazolyl-2-oxy)phenoxy]-2-hexanone.
24. 4-hydroxy-5-[4-(6-chloro benzo-1,3-oxazolyl-2-oxy)phenoxy]-2-hexanone.

EXAMPLE 6

To a solution of 3-[4-(4-trifluoromethylphenoxy)phenoxy]-2-butanone N,N-dimethylhydrazone (5.4 mmol) in THF (15 ml) under nitrogen is added lithium diisopropylamide (6.6 mmol) in THF (15 ml) at 0° for 4 hours. The resulting solution is cooled to −78°, and to it is added ethanal (6.6 mmol). After 1 hour at −78°, the reaction mixture is allowed to warm to 0° and is poured into water/methylene chloride (3:1). The organic phase is separated (3X), and the combined organic extracts are dried over sodium sulfate and concentrated to give 5-hydroxy-2-[4-(4-trifluoromethylphenoxy)phenoxy]-3-hexanone N,N-dimethylhydrazone (cpd. 25, Table C).

The above hexanone N,N-dimethylhydrazone (1 mmol) is dissolved in methanol (15 ml) and 1.0 N pH 7 phosphate buffer (3 ml), and a solution of sodium periodate (2.2 mmol) in water (5 ml) is added at 25° with stirring. After about 3 hours, the reaction mixture is filtered, poured into water and extracted with methylene chloride. The extract is dried and concentrated in vacuo to give 5-hydroxy-2-[4-(4-trifluoromethylphenoxy)phenoxy]-3-hexanone (cpd. 25, Table D).

EXAMPLE 7

Following the procedure of Example 6, the lithium salt of each of the hydrazones under column V is reacted with ethanal to give the corresponding compound in Table C, which is then hydrolyzed to the corresponding ketone in Table D.

V 26. 3-[4-(2-chloro-4-trifluoromethylphenoxy)phenoxy]-2-butanone N,N-dimethylhydrazone.
27. 3-[4-(2-nitro-4-trifluoromethylphenoxy)phenoxy]-2-butanone N,N-dimethylhydrazone.
28. 3-[4-(2,4-dichlorophenoxy)phenoxy]-2-butanone N,N-dimethyl-hydrazone.
29. 3-[4-(4-trifluoromethylphenylthio)phenoxy]-2-butanone N,N-dimethylhydrazone.
30. 3-[4-(2-nitro-4-trifluoromethylanilino)phenoxy]-2-butanone N,N-dimethylhydrazone.
31. 3-[4-(4-trifluoromethylphenoxy)phenoxy]acetone N,N-dimethylhydrazone.

EXAMPLE 8

Following the procedure of Example 6, the lithium salt of 3-[4-(4-trifluoromethylphenoxy)phenoxy]-2-butanone N,N-dimethylhydrazone is prepared and reacted with propanal to give 5-hydroxy-2-[4-(4-trifluoromethylphenoxy)phenoxy]-3-heptanone N,N-dimethylhydrazone (cpd. 32, Table C), which is then hydrolyzed to the corresponding 3-heptanone (cpd. 32, Table D).

EXAMPLE 9

Following the procedure of Example 4, 5-hydroxy-2-[4-(4-trifluoromethylphenoxy)phenoxy]-3-hexanone is reacted with each of 2,2-dichloropropionyl chloride, 4-(2,4-dichlorophenoxy)butyryl chloride and ethoxycarbonyl chloride to yield the corresponding 5-substituted hexanones in Table D (compounds 33, 34 and 35, respectively).

TABLE C

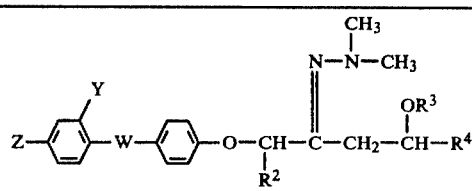

| Cpd | Z | Y | W | R² | R³ | R⁴ |
|---|---|---|---|---|---|---|
| 25 | $CF_3$ | H | O | $CH_3$ | H | $CH_3$ |
| 26 | $CF_3$ | Cl | O | $CH_3$ | H | $CH_3$ |
| 27 | $CF_3$ | $NO_2$ | O | $CH_3$ | H | $CH_3$ |
| 28 | Cl | Cl | O | $CH_3$ | H | $CH_3$ |
| 29 | $CF_3$ | H | S | $CH_3$ | H | $CH_3$ |
| 30 | $CF_3$ | $NO_2$ | NH | $CH_3$ | H | $CH_3$ |
| 31 | $CF_3$ | H | O | H | H | $CH_3$ |
| 32 | $CF_3$ | H | O | $CH_3$ | H | $CH_2CH_3$ |

TABLE D

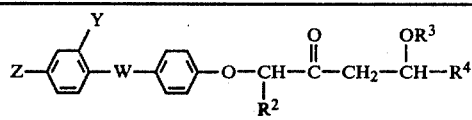

| Cpd | Z | Y | W | R² | R³ | R⁴ |
|---|---|---|---|---|---|---|
| 25 | $CF_3$ | H | O | $CH_3$ | H | $CH_3$ |
| 26 | $CF_3$ | Cl | O | $CH_3$ | H | $CH_3$ |
| 27 | $CF_3$ | $NO_2$ | O | $CH_3$ | H | $CH_3$ |
| 28 | Cl | Cl | O | $CH_3$ | H | $CH_3$ |
| 29 | $CF_3$ | H | S | $CH_3$ | H | $CH_3$ |
| 30 | $CF_3$ | $NO_2$ | NH | $CH_3$ | H | $CH_3$ |
| 31 | $CF_3$ | H | O | H | H | $CH_3$ |
| 32 | $CF_3$ | H | O | $CH_3$ | H | $CH_2CH_3$ |
| 33 | $CF_3$ | H | O | $CH_3$ | $C(O)C(Cl)_2CH_3$ | $CH_3$ |
| 34 | $CF_3$ | H | O | $CH_3$ | $C(O)(CH_2)_3OC_6H_3$—(2,4-diCl) | $CH_3$ |
| 35 | $CF_3$ | H | O | $CH_3$ | $C(O)OCH_2CH_3$ | $CH_3$ |

EXAMPLE 10

Following the procedure of Example 6, ethanal is reacted with the lithium salt of each of 3-[4-(5-trifluoromethyl-2-pyridyloxy)phenoxy]-2-butanone N,N-dimethylhydrazone and 3-[4-(3-chloro-5-trifluoromethyl-2-pyridyloxy)phenoxy]-2-butanone N,N-dimethylhydrazone to give the N,N-dimethylyhydrazone of the β-hydroxy ketone, which is then hydrolyzed to the following respective ketones:

5-hydroxy-2-[4-(5-trifluoromethyl-2-pyridyloxy)-phenoxy]-3-hexanone, and 5-hydroxy-2-[4-(3-chloro-5-trifluoromethyl-2-pyridyloxy)-phenoxy]-3-hexanone.

What is claimed is:

1. A compound of the following formula:

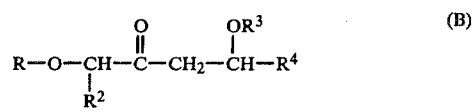

(B)

-continued wherein,

R is 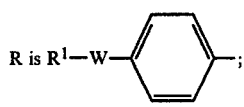

$R^1$ is 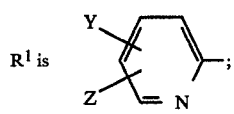

$R^2$ is hydrogen or lower alkyl;
$R^3$ is hydrogen, lower alkyl,

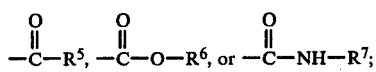

$R^4$ is lower alkyl;
$R^5$ is lower alkyl, lower haloalkyl, substituted or unsubstituted phenyl, substituted or unsubstituted benzyl, or substituted or unsubstituted phenoxyloweralkyl;
$R^6$ is lower alkyl;
$R^7$ is hydrogen, lower alkyl or substituted or unsubstituted phenyl;
W is oxygen; and
each of Y and Z is independently hydrogen, lower alkyl, lower haloalkyl, or halogen, wherein substituted phenyl, substituted benzyl and substituted/-phenoxy loweralkyl are substituted with one, two or three substituents selected from lower alkyl, lower haloalkyl, lower alkoxy, halogen, nitro or cyano at ring carbon atoms.

2. A compound of the following formula, according to claim 1:

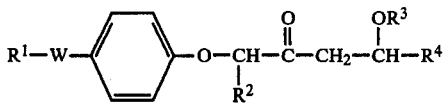

3. A compound of the following formula, according to claim 2:

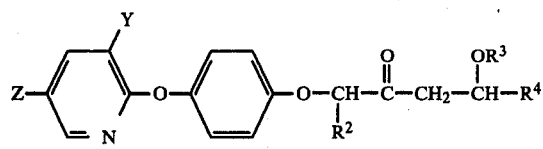

4. A compound according to claim 3 wherein $R^2$ is methyl, $R^4$ is methyl or ethyl, Y is hydrogen or chloro and Z is chloro or trifluoromethyl.

5. A compound according to claim 4 wherein $R^3$ is hydrogen.

6. A compound according to claim 4 wherein $R^3$ is methyl or ethyl.

7. A compound according to claim 4 wherein $R^3$ is $$-\overset{O}{\underset{\|}{C}}-R^5$$

where $R^5$ is methyl, ethyl, 1,1-dichloroethyl or dichlorophenoxypropyl.

* * * * *